United States Patent [19]

Branemark et al.

[11] 4,065,817
[45] Jan. 3, 1978

[54] BONE PROSTHESIS AND METHOD OF FORMING A BONE JOINT

[76] Inventors: Per Ingvar Branemark, Andergatan 3; Bo Thuresson Af Ekenstam, Akergatan 5,, both of S-431 39 Molndal, Sweden

[21] Appl. No.: 679,709

[22] Filed: Apr. 23, 1976

[51] Int. Cl.² ............................................. A61F 1/24
[52] U.S. Cl. ........................................ 3/1.91; 3/1.912; 128/92 C
[58] Field of Search ............................. 3/1, 1.9–1.913; 128/92 C, 92 CA; 32/10 A

[56] References Cited

U.S. PATENT DOCUMENTS

| | | | |
|---|---|---|---|
| 2,857,670 | 10/1958 | Kiernan | 32/10 A |
| 3,435,526 | 4/1969 | Brancato | 32/10 A |
| 3,657,744 | 4/1972 | Ersek | 3/1 |
| 3,848,272 | 11/1974 | Noiles | 3/1.913 |

FOREIGN PATENT DOCUMENTS

| | | | |
|---|---|---|---|
| 2,404,214 | 8/1974 | Germany | 3/1.9 |
| 1,961,531 | 9/1970 | Germany | 3/1 |
| 2,314,708 | 10/1974 | Germany | 3/1.912 |

Primary Examiner—Ronald L. Frinks

[57] ABSTRACT

A bone prosthesis and the method of securing it in place, in which the prosthesis is formed as a tubular support member having perforations therein, the end of the bone is bored, the tubular support member is introduced into the bore and cement is then introduced into the interior of the tubular support and passes out through the perforations to provide the midterm anchor on the walls of the bone. The cement will damage the tissue where it contacts the tissue, but the remainder of the tissue of the bore is undamaged and this grows inwardly to form a long term anchor between the tubular support and the bone. A prosthesis body is located and secured in place e.g. mechanically or by cement, in the tubular support member.

12 Claims, 8 Drawing Figures

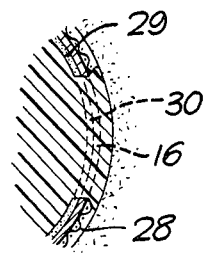
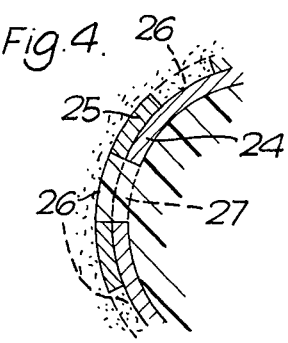
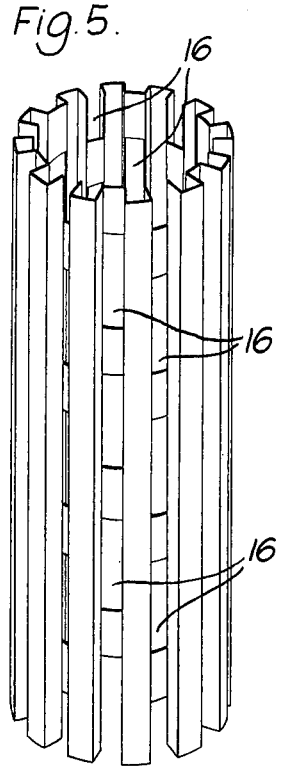
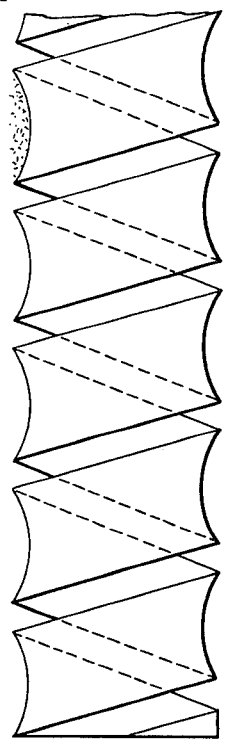

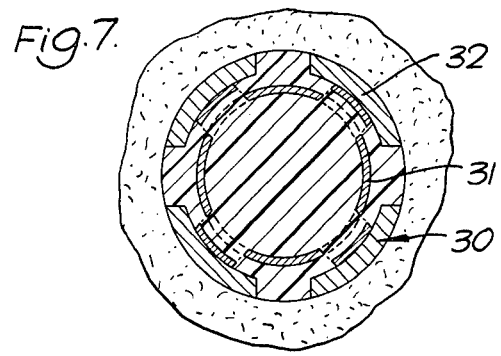
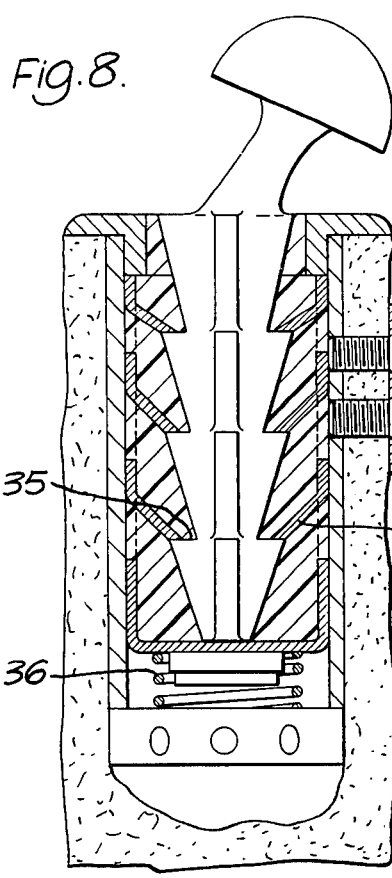

BONE PROSTHESIS AND METHOD OF FORMING A BONE JOINT

The present invention relates to a bone prosthesis and a method of forming a bone joint utilizing such a prosthesis.

It is known to permanently reconstruct the bone joints of a human which are malformed either from birth, or due to disease or accident, by various means.

One technique involves the substitution of the components of a joint from a biologically acceptable material such as metal or plastics which is inserted in a bore formed in the ends of the bone and is held in place by a cementing procedure. The conventional form of cement utilized are plastics material cement, based on modern polymers which are capable of forming organic-chemical monomers. These cements are prepolymerized in order to ensure sufficient plasticity for putting them in place. However, when the cements are finally cured, they need to be raised to a high reaction temperature and this, together with the side effects produced by the monomers has a disadvantageous biological effect on the bone, killing the bone tissue. Thus, this technique although it is satisfactory in the short term is not suitable for long term use.

The modern prosthetic devices themselves have been satisfactorily manufactured from biologically compatible metal such as titanium and titanium alloys or vitallium. Plastics materials are also used to form the components of the prosthesis themselves, although these are normally only suitable for smaller joints, such as finger joints. The actual retention of the device in the bone is a function of the cement itself, and it has been conventional to use methyl acrylic and polymethyl acrylic, or methyl methacrylic styrene copolymers with or without the addition of barium sulphate.

As mentioned, the bond provided previously is not entirely satisfactory for the reasons outlined.

According to the present invention, we provide a bone prosthesis comprising a tubular support member having a plurality of lateral openings disposed at spaced locations along the length and around the periphery of the support member through the wall thereof, the prosthesis body locatable at least in part in said support member and means for securing the body in place in the support body.

With such a prosthesis, the bone to be treated is boned out as is conventional, and the tubular support member is inserted in place. A suitable cement of the kind mentioned above is introduced into the tubular support member so that it passes locally through the openings and contact the bore at the location of these openings only. The cement is cured, the prosthesis body is either prior to this curing or during this curing located and secured in place in the tubular support member.

With such an arrangement, the only portion of the bone tissue which is in any way damaged is that portion which is touched by the cement. The cement serves to hold the tubular support member in position for a short term or midterm period. This is sufficient to allow the bone tissue to grow inwardly and anchor the remainder of the tubular support member in place. Thus, when the bond between the cement and the bone breaks down, as it will in due course, the tissue will hold the support member in place.

The tubular support member may take a number of different forms and may, for example, comprise an inner tube and an outer tube, the outer tube having a plurality of lateral openings through the wall thereof, and the inner tube having a smaller number of openings therein, these openings being in register with the openings of the outer tube. The cement passes through the registering openings and the other openings serve to assist in anchoring the support member to the tissue when it grows. In another construction, the support member may comprise a mesh material which again forms a good anchor for the growing tissue. The inner surface of the mesh material may be formed with a wall of ceramic material having holes therein in register with the lateral openings and this serves to form a heat barrier to the heat of the cement.

The tube may be formed to have an inner portion and an outer portion by punching so that the cement executed a tortuous path from the interior to the exterior and provides a better bond.

The tubular support member may, alternatively, be formed of a helix, and in any of the constructions may be radially expansible.

Various means may be provided for securing the body of the prosthesis to the tubular support member, for example radially inwardly extending projections may be provided from the interior of the support member and these may cooperate with members on the prosthesis body itself.

In order that the invention may be more readily understood, the following description is given, merely by way of example, reference being made to the accompanying drawings, in which:

FIGS. 3 and 4 are end views of two further embodiments of support tube;

FIGS. 5 and 6 are elevations of two further forms of support tube;

FIG. 7 is a transverse section of a further embodiment of support tube; and

FIG. 8 illustrates a modified construction of prosthesis showing the method of holding the prosthesis member in place.

Figure 1:
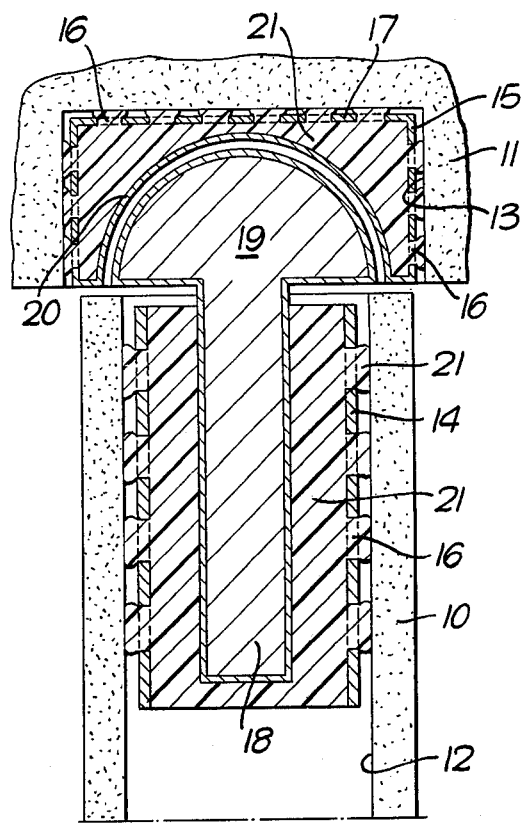
FIG. 1 is a section through a pair of bones provided with a prosthesis joint according to the invention.

Referring now to FIG. 1 of the drawings there is illustrated two portions of bone 10 and 11 to be secured together by a ball and socket type joint. The bones 10 and 11 are provided with bores 12 and 13 respectively and a tubular support member 14 is inserted in the bore 12 and a further tubular support member 15 in the bore 13.

The tubular support member 14 and 15 are each provided with a plurality of lateral openings 16 which are disposed at spaced locations both along the length and around the periphery of the support member. The support member 15 has a closed end 17 which is also provided with similar openings 16.

A prosthesis body having a stem 18 and a head 19 is inserted with the stem into the support member 16. A complementary prosthesis in the form of a cup 20 is inserted in the bore 13.

Cement of the type described earlier is introduced into the space between the stem and support member and the space between the member 20 and the support member 15, and is forced in through the openings 16 into contact with the wall of the bore adjacent these openings only. The remainder of the bore is not contacted by the cement.

The cement serves to secure the support member in place for a short term or mid-term period. The bone tissue at these locations is killed either by the temperature of the cement or by the chemical reaction thereof. However, this is sufficient to hold the prosthesis in place for a period of time. During this period of time the bone tissue which has not been killed, that is the material opposite the unperforated portion of the support, grows inwardly and anchors the support firmly on a permanent basis. The cement also serves to hold the prosthesis member 18, 19, 20 in position.

Figure 2:
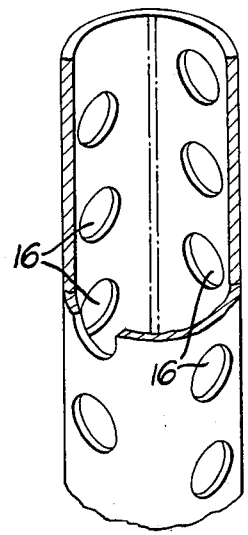
FIG. 2 is a perspective view of the support member of the device of FIG. 1.

As can be seen from FIG. 2 the holes 16 are arranged along a helix. The holes shown are round, although these may be of any other shape, for example, elongate slots.

As seen in FIG. 3, a tubular support member comprises a mesh material 28, with a plurality of lateral openings 16 therein, and a wall of ceramic materials 29 provided with holes 30 therein.

The construction illustrated in FIG. 4 has an inner tube 24 and an outer tube 25, the outer tube having a plurality of openings 26 therein through the wall thereof and the inner tube having a smaller number of openings 27, these openings being in register with the openings of the outer tube. Thus, the remaining openings of the outer tube form an anchoring point for the bone tissue.

FIG. 5 shows a further form of support tube which is radially expansible and being provided with a crenalated periphery in which the openings 16 are formed.

In the construction of FIG. 6 the support is formed as a helix, the initial diameter of which is slightly larger than the bore but it can be radially contracted by twisting. This forms a further mechanical anchor on the bore. The opening can be considered as laterally spaced between turns, although in fact it is a continuous helix.

FIG. 7 shows a further form of tube 30 having an inner portion 31 and an outer portion 32 formed by punching the outer tube outwardly from the inner tube. In this way the apertures formed are not aligned and the cement is caused to execute a somewhat tortuous path between the two tubes on its way from the interior to contact with the bore in the bone.

FIG. 8 shows a further construction in which the support tube is provided with radially inwardly extending projections 34 and cooperating members 35 on the prosthesis body. A spring 36 is provided at the end to reduce axial shocks.

We claim:
1. A bone prosthesis comprising, in combination:
   a. a tubular support member;
   b. a plurality of lateral openings disposed at spaced locations along the length and around the periphery of said support member and through the wall thereof;
   c. a prosthesis body having at least a part locatable in part in said tubular support member, said part having an outer surface dimensioned to be spaced from the inner surface of said tubular support member, whereby bone cement can be introduced into said tube support member when the prosthesis body is in place and flows through said lateral openings: and
   e. means for securing said body in place in said support member.

2. A prosthesis as claimed in claim 1, wherein the tubular support member comprises an inner tube and an outer tube, the outer tube having a plurality of lateral openings through the wall thereof, and the inner tube having a smaller number of openings therein, these openings being in register with the openings of the outer tube.

3. A prosthesis as claimed in claim 1, wherein the tubular support member comprises a mesh material with a plurality of lateral openings therethrough.

4. A prosthesis as claimed in claim 3, and further comprising, on the inner surface of said mesh material, a wall of ceramic material having holes therein in register with the lateral openings.

5. A prosthesis as claimed in claim 1, wherein the tubular support member comprises a tube having an inner portion and an outer portion radially spaced therefrom by punching.

6. A prosthesis as claimed in claim 1, wherein the tubular support member is formed as a helix.

7. A prosthesis as claimed in claim 1, wherein the tubular support member is radially resilient.

8. A prosthesis as claimed in claim 7, wherein the tubular support member has a crenelated periphery.

9. A prosthesis as claimed in claim 1, wherein the means for securing the body in place comprise radially inwardly extending projections on the tubular support member and co-operating members on the prosthesis body.

10. A bone prosthesis comprising, in combination:
   a. a tubular support member formed of mesh material providing a plurality of lateral openings disposed at spaced locations along the length and around the periphery of said support member and through the wall thereof;
   b. a wall of ceramic material having holes therein in register with the lateral openings disposed on the inner surface of said mesh material;
   c. a prosthesis body having at least a part locatable in said tubular mesh support member; and
   d. means for securing said body in place in said support member.

11. A bone prosthesis comprising in combination:
   a. a tubular support member comprising a tube having an inner portion and an outer portion radially spaced therefrom by punching;
   b. a plurality of lateral openings disposed at spaced locations along the length and around the periphery of said support member and through the wall thereof;
   c. a prosthesis body having at least a part locatable in said inner portion of said tube; and
   d. means for securing said body in place in said inner portion of the tubular support member.

12. A method of forming a bone joint comprising:
   a. providing a tubular support member having a plurality of lateral openings disposed at spaced locations along the length and around the periphery of said support member and through the wall thereof;
   b. forming a bore in the end of a bone to be joined;
   c. inserting the tubular support member in the bore;
   d. introducing cement into said tubular support member, whereby it passes locally through said openings to contact spaced portions of said bore only;
   e. curing said cement; and
   f. locating and securing a prosthesis body in said tubular support member.

* * * * *